United States Patent
Scheib

(10) Patent No.: US 7,618,430 B2
(45) Date of Patent: Nov. 17, 2009

(54) RETRACTABLE DILATOR NEEDLE

(75) Inventor: Mark S. Scheib, La Verne, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 199 days.

(21) Appl. No.: 10/118,679

(22) Filed: Apr. 9, 2002

(65) Prior Publication Data

US 2003/0163153 A1 Aug. 28, 2003

Related U.S. Application Data

(60) Provisional application No. 60/360,694, filed on Feb. 28, 2002.

(51) Int. Cl.
*A61M 29/00* (2006.01)

(52) U.S. Cl. .................. 606/191; 606/181; 606/194; 604/164.1

(58) Field of Classification Search ............... 606/191, 606/185, 194; 128/898; 604/164.01
See application file for complete search history.

(56) References Cited

U.S. PATENT DOCUMENTS

| | | | | |
|---|---|---|---|---|
| 4,994,079 A | * | 2/1991 | Genese et al. | 606/206 |
| 5,311,858 A | * | 5/1994 | Adair | 600/106 |
| 5,312,341 A | * | 5/1994 | Turi | 604/103.05 |
| 5,360,432 A | * | 11/1994 | Shturman | 606/159 |
| 5,797,960 A | * | 8/1998 | Stevens et al. | 606/213 |
| 6,120,494 A | | 9/2000 | Jonkman | |
| 6,254,599 B1 | | 7/2001 | Lesh et al. | |
| 6,293,952 B1 | * | 9/2001 | Brosens et al. | 606/119 |
| 6,299,603 B1 | | 10/2001 | Hecker et al. | |
| 6,641,564 B1 | * | 11/2003 | Kraus | 604/164.1 |
| 6,650,923 B1 | * | 11/2003 | Lesh et al. | 600/407 |
| 6,662,045 B2 | * | 12/2003 | Zheng et al. | 607/5 |
| 6,679,268 B2 | * | 1/2004 | Stevens et al. | 128/898 |

\* cited by examiner

*Primary Examiner*—Darwin P Erezo
(74) *Attorney, Agent, or Firm*—Christie, Parker & Hale, LLP

(57) ABSTRACT

A dilator having a retractable needle is disclosed. The dilator includes an elongated dilator body having a proximal end, a distal end and at least one lumen longitudinally extending therethrough. A handle is mounted at the proximal end of the dilator body, and a control button is moveably connected to the outside of the handle. The needle extends through the lumen and has a distal end comprising a needle tip section. An arm attached the control button to the needle. Distal movement of the control button causes the needle to move from a retracted position, wherein the needle tip is disposed within the lumen of the dilator body, to a protruding position, wherein the needle tip protrudes beyond the distal end of the dilator body. In use, the distal end of the dilator is inserted into the right atrium of a patient, a position on the atrial septum to be punctured is located with the distal end of the dilator body, the needle tip is advanced beyond the distal end of the dilator body, and the atrial septum is punctured with the needle tip.

13 Claims, 4 Drawing Sheets

RETRACTABLE DILATOR NEEDLE

CROSS-REFERENCE TO RELATED APPLICATION

This application claims priority of U.S. Provisional Patent Application No. 60/360,694, filed Feb. 28, 2002, the disclosure of which is incorporated herein by reference.

FIELD OF THE INVENTION

The present invention is directed to a dilator. More particularly the present invention is directed to a dilator having a retractable needle.

BACKGROUND OF THE INVENTION

Electrophysiology catheters are commonly used for mapping electrical activity in a heart. Electrophysiology is a specialty within the field of cardiology for diagnosis and treatment of electrical abnormalities of the heart. By mapping the electrical activity in the heart, ectopic sites of electrical activation or other electrical activation pathways that contribute to heart malfunctions may be detected. This type of information may then allow a cardiologist to intervene and destroy the malfunctioning heart tissues. Such destruction of heart tissue is typically performed using an ablation catheter and is referred to as ablation. Ablation is a rapidly growing field within electrophysiology and obviates the need for maximally invasive open heart surgery.

Occasionally, an electrical abnormality occurs in a location that is difficult to reach with standard catheter capabilities. A left atrium of a heart is one such location. When an electrical abnormality occurs in a left atrium, a dilation catheter, or dilator, may be inserted percutaneously, fed through one or more major blood vessels, and inserted into a right atrium of the heart. A needle may then be feed through the dilator and inserted into and through the atrial septum to puncture the atrial septum to allow access to the left atrium for a therapeutic catheter, such as an ablation catheter.

A current technique for puncturing the atrial septum includes positioning a dilator adjacent to an area of the atrial septum that is desired to be punctured, inserting a separate needle into the dilator, feeding the needle through the dilator until the needle protrudes beyond the dilator, and puncturing the atrial septum with the needle. This technique has several disadvantages. For example, locating the desired puncture site and then inserting and feeding a separate needle into the dilator increases the procedure time, and increases the likelihood that the dilator will be inadvertently moved before the needle reaches the desired puncture site, thus requiring a repositioning of the dilator. If the repositioning is performed with the needle inside the dilator, the possibility exists for the needle to slide out of the dilator and damage venous or atrial structures. If the needle is removed during repositioning, procedure time is again extended during reinsertion and re-feeding of the needle into the dilator, and an inadvertent movement of the dilator during reinsertion and re-feeding of the needle again exists.

Another more serious disadvantage of the current technique is that a force in a distal direction is required to insert the needle into and through the atrial septum, yet there is no means for controlling the maximum protrusion of the needle from the dilator. As a result, a tendency is for the operator to continue to apply a forward force to the needle even after the needle has crossed the atrial septum, thus risking damage to venous or atrial structures in the left atria or even cardiac puncture if the needle protrudes too far from the dilator.

SUMMARY OF THE INVENTION

In an exemplary embodiment, the present invention addresses the above-referenced problems by providing a dilator having an elongated dilator body having a proximal end, a distal end and at least one lumen longitudinally extending therethrough, a handle mounted at the proximal end of the dilator body, a control button moveably connected to the outside of the handle, a needle extending through the lumen of the dilator body, the needle having a distal end comprising a needle tip section and a proximal end, and an arm connecting the control button to the needle, wherein distal movement of the control button relative to the handle and dilator body causes the needle to move from a retracted position, wherein the needle tip is disposed within the lumen of the dilator body, to a protruding position, wherein the needle tip protrudes beyond the distal end of the dilator body.

Another embodiment of the present invention includes inserting the distal end of the dilator into the right atrium of a patient, locating a position of the atrial septum to be punctured, advancing the needle tip distally beyond the distal end of the dilator body, and puncturing the atrial septum with the needle tip.

DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

The invention is directed to a dilation catheter, or dilator, having a needle for use in puncturing an internal bodily membrane, such as the atrial septum. The needle is movable relative to the dilator such that the needle may be adjusted between a retracted position, wherein a distal tip section of the needle is disposed within the dilator, and a protruding position, wherein the tip section of the needle protrudes beyond the dilator. Attached to a distal end of the dilator is a handle, having a thumb control or other similar moveable member. The thumb control is connected to the needle at or near the needle's proximal end by means of an arm, such that the needle may be adjusted between the retracted position and the protruding position by longitudinally manipulating the thumb control.

Figure 1:
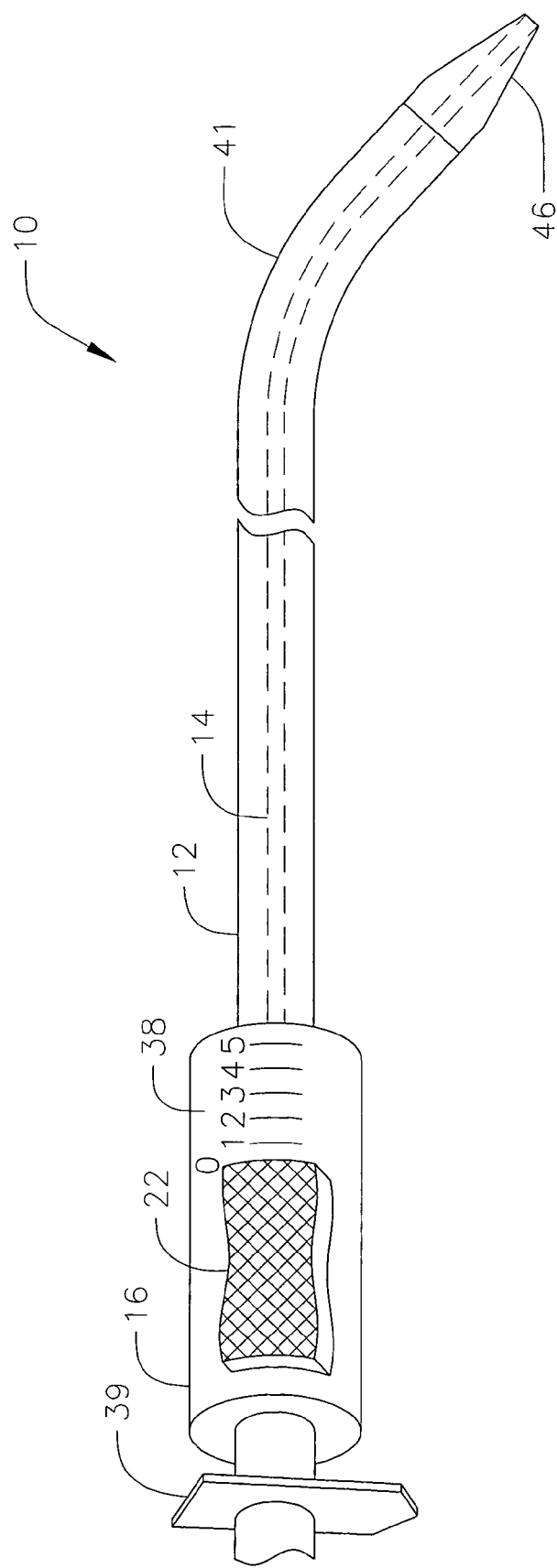
FIG. 1 is a perspective view of a dilator according to the invention.
Figure 2A:
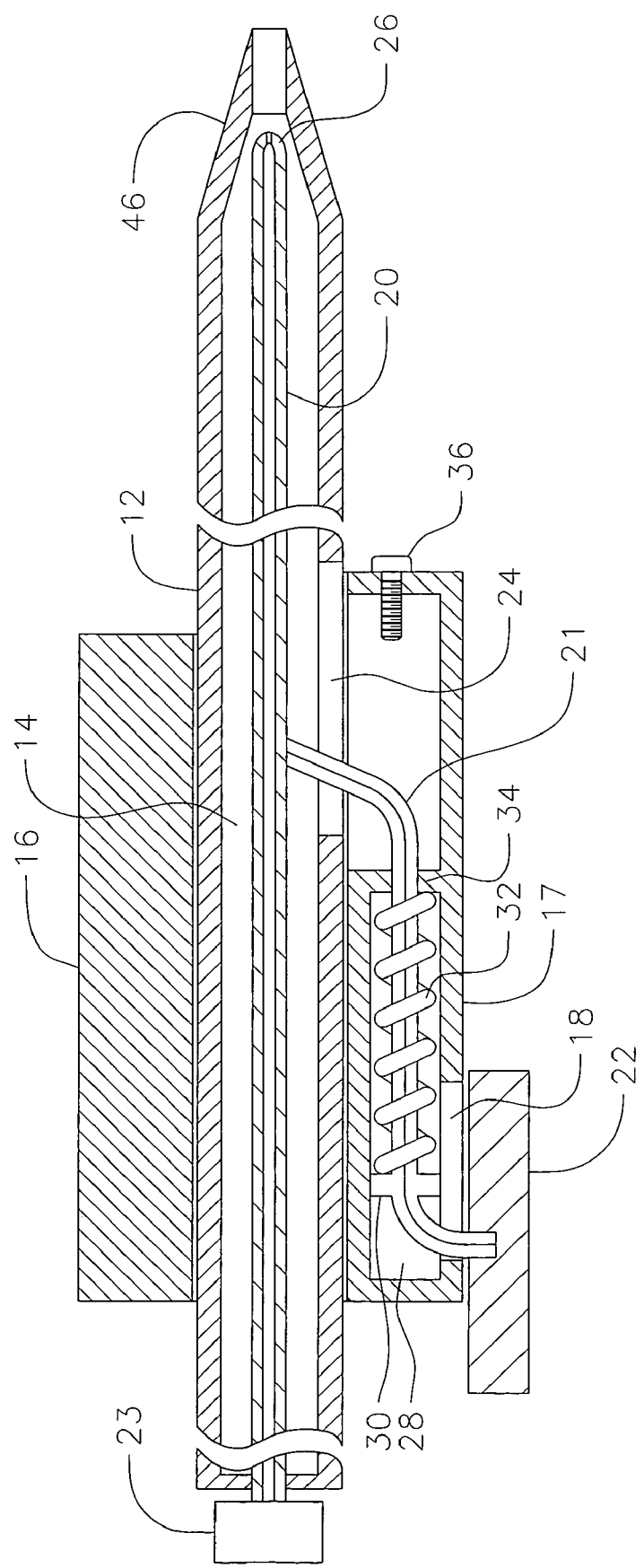
FIG. 2A is a longitudinal cross-sectional view of the dilator of FIG. 1, showing a needle in a retracted position.
Figure 2B:
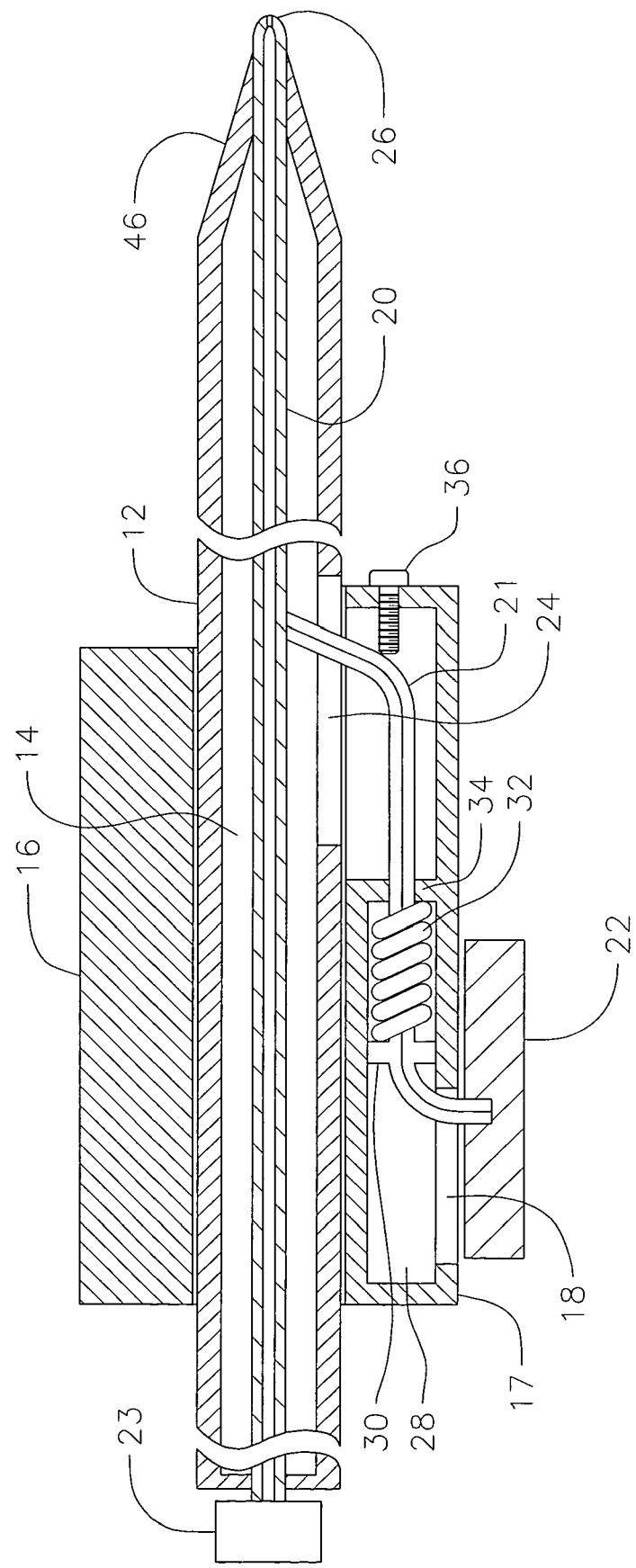
FIG. 2B is a longitudinal cross-sectional view of the dilator of FIG. 1, showing a needle in a protruding position.

A dilator 10 of the present invention is shown in FIGS. 1 to 2B. The dilator 10 comprises an elongated tubular body 12 having a proximal end, a distal end and at least one lumen 14 longitudinally extending therethrough. In the depicted embodiment, the lumen 14 is a central lumen. An elongated needle 20 extends through the lumen 14 of the dilator 10.

Attached to the proximal end of the dilator body 12 is a handle 16. The dilator body 12 can be of any suitable construction. Preferably the dilator body 12 comprises polyethylene with barium sulfate. It is also preferred that a coating is provided over the dilator body 12 to provide lubricity when the dilator is placed within a guiding sheath. A suitable coating comprises silicone, such as MDX4-4159, a mixture of aminofunctional polydimethylsiloxane copolymer in mixed aliphatic and isopropanol solvents (commercially available from Dow Corning™, Midland, Mich.). The dilator body 12 has an outer diameter ranging from about 0.075 inch to about 0.150 inch, preferably from about 0.103 inch to about 0.109 inch, more preferably about 0.106 inch, and an inner diameter sufficient to receive a needle (described below). Preferably the dilator body 12 has a length ranging from about 60 cm to about 100 cm.

The distal end of the dilator body 12 can be straight. However, in some instances it may be advantageous for a portion of the distal end of the dilator body 12 to have a pre-formed curve, shown in FIG. 1 as curved section 41. For example, due to the angle of the right atrium opening with respect to the atrial septum, when a dilator body having a straight distal end is inserted into the right atrium and advanced to a position adjacent to the atrial septum, the distal tip of the dilator is likely to be angled with respect to the atrial septum. In such an instance, it may be desirable for the distal end of the dilator body 12 to have a pre-formed curve to allow the distal tip of the dilator body to point more perpendicularly to the atrial septum, thus allowing for a cleaner puncture of the septum.

In embodiments where the distal end of the dilator body contains the curved section 41, a pointer 39 may be attached to the proximal end of the dilator body 12. The pointer 39 points in the direction of the curve of the curved section 41. The pointer 39 is fixedly attached to the proximal end of the dilator body 12 such that when the curved section 41 of the dilator body 12 rotates, the pointer correspondingly rotates, thus allowing the rotational orientation of the curved section to be continually monitored from outside the body.

The handle 16 can be made of any suitable material. Preferably, the handle 16 comprises a rigid plastic material, such as Delrin. The handle 16 is attached to the proximal end of the dilator body 12, for example, by using a polyurethane glue or the like and is preferably mounted in surrounding relation to the dilator 10. In the depicted embodiment, the handle 16 is generally cylindrical with a round sidewall 17. The handle 16 contains an opening or slot 18 in the sidewall 17.

A thumb control 22 is moveably connected to the handle 16 for manipulation of the needle 20. Preferably, the thumb control 22 is connected to the outside of the handle 16. An arm 21 connects the thumb control 22 to the needle 20. As will become apparent to one skilled in the art, the thumb control 22 can be integral with the arm 21 or it can be a separate component. The arm 21 extends through the slot 18 in the sidewall 17 of the handle 16. In the depicted embodiment, the arm 21 has a proximal end joined to the thumb control 22, although the thumb control can alternatively be attached to any other point along the arm. In the depicted embodiment, a distal end of the arm 21 extends through a slot 24 in the dilator body 12, and into the dilator lumen 14 where it is attached at or near the proximal end of the needle 20. The arm 21 may be attached to the needle 20 in a variety of ways such as by press fitting, glueing, or screw fastening, among other methods. Alternatively, the arm 21 can be formed as a single piece with the needle 20 so that it is integral with the needle. With the above-described depicted and alternative embodiments, longitudinal movement of the thumb control 22 causes a corresponding movement of the needle relative to the handle 16 and the dilator body 12.

A distal end of the needle 20 converges to form a tip section 26, having a pointed end suitable for puncturing a bodily membrane, such as an atrial septum. The needle 20 may comprise any material suitable for cleanly puncturing a bodily membrane. Preferably, the needle 20 is comprised of a metal, such as stainless steel. An outer diameter of the needle preferably ranges from about 0.020 inches to about 0.040 inches, and more preferably is about 0.035 inches. In a retracted position (shown in FIG. 2A), the needle tip 26 is contained within the dilator body, and in a protruding position (shown in FIG. 2B), the needle tip protrudes beyond the distal end 46 of the dilator body 12. Preferably, when the needle tip 26 is in the retracted position, the needle tip is disposed near the distal end 46 of the dilator body 12 such that when it is desired to advance the needle tip 26 beyond the distal end 46 of the dilator body 12, a distance between the needle tip and the distal end of the dilator body is small, resulting in a reduced procedure time. For example, when the needle tip 26 is in the retracted position, the needle tip may be disposed 1 mm, 5 mm, 1 cm, 5 cm or any other suitable dimension from the distal end 46 of the dilator body 12.

In a preferred embodiment, the needle 20 is hollow and its proximal end extends beyond the proximal end of the dilator body 12. A pressure valve 23 is mounted on the needle 20 at or near the needle's proximal end such that the pressure in the needle may be monitored, as discussed further below.

The arm 21 is attached to the needle 20 such that a movement of the thumb control 20 causes a corresponding movement of the needle tip 26 relative to the dilator body 12. Consequently, the needle tip 26 may be adjusted between the retracted position and the protruding position by manipulating the thumb control 22. In use, the dilator 10 is inserted into a patient percutaneously, fed through one or more major blood vessels and disposed adjacent to a membrane desired to be punctured. When the operator is prepared to puncture the membrane, the operator may move the thumb control 22 distally such that the needle tip 26 is in the protruding position. It is preferred that the needle tip 26 is biased, locked or otherwise held in the retracted position during transport of the dilator 10 through the venous system and during positioning of the dilator adjacent to the membrane to be punctured. If the needle tip 26 is not biased or otherwise locked in the retracted position during the transport and positioning of the dilator 10, then a danger exists that the needle tip 26 will inadvertently protrude from the dilator and damage venous or atrial structures. Consequently, in a preferred embodiment, the thumb control 22 is biased in a proximal direction, such that the needle tip 26 is biased in the retracted position.

Biasing of the needle tip 26 can be accomplished in a variety of ways, such as in the depicted embodiment of FIGS. 2A and 2B. In the depicted embodiment, the handle 16 has a channel 28, through which the arm 21 extends. Within the channel 28, the arm 21 has a shoulder 30, which may be formed by machining or by affixing a washer to the arm, among other methods. A spring 32, such as a compression spring, is disposed between the arm shoulder 30 and a distal end or distal shoulder 34 of the channel 28. Preferably, the spring 32 is disposed in surrounding relation to the arm 21. The spring 32 biases the arm 21, and therefore the thumb control 22, in a proximal direction. When an operator desires to move the needle 20 into the protruding position, the operator applies a force to the thumb control 22 to distally move the thumb control, causing a corresponding distal movement of the needle as well. This results in a compression of the spring 32, such that when the thumb control 22 is released, the spring 32 applies a force to the arm shoulder 30 to return the needle 20 to the retracted position.

As shown in FIG. 1, the handle 16 may contain reference marks 38 indicative of the extent of the protrusion of the needle tip 26. In the depicted embodiment, the reference marks are painted lines that do not impede the motion of the thumb control 22. Alternatively, a distal end of the thumb control 22 may contain a downward projecting spring and the reference marks 38 may be a series of grooves such that the operator can position the distal end of the thumb control within any one of the reference mark grooves.

Figure 3:
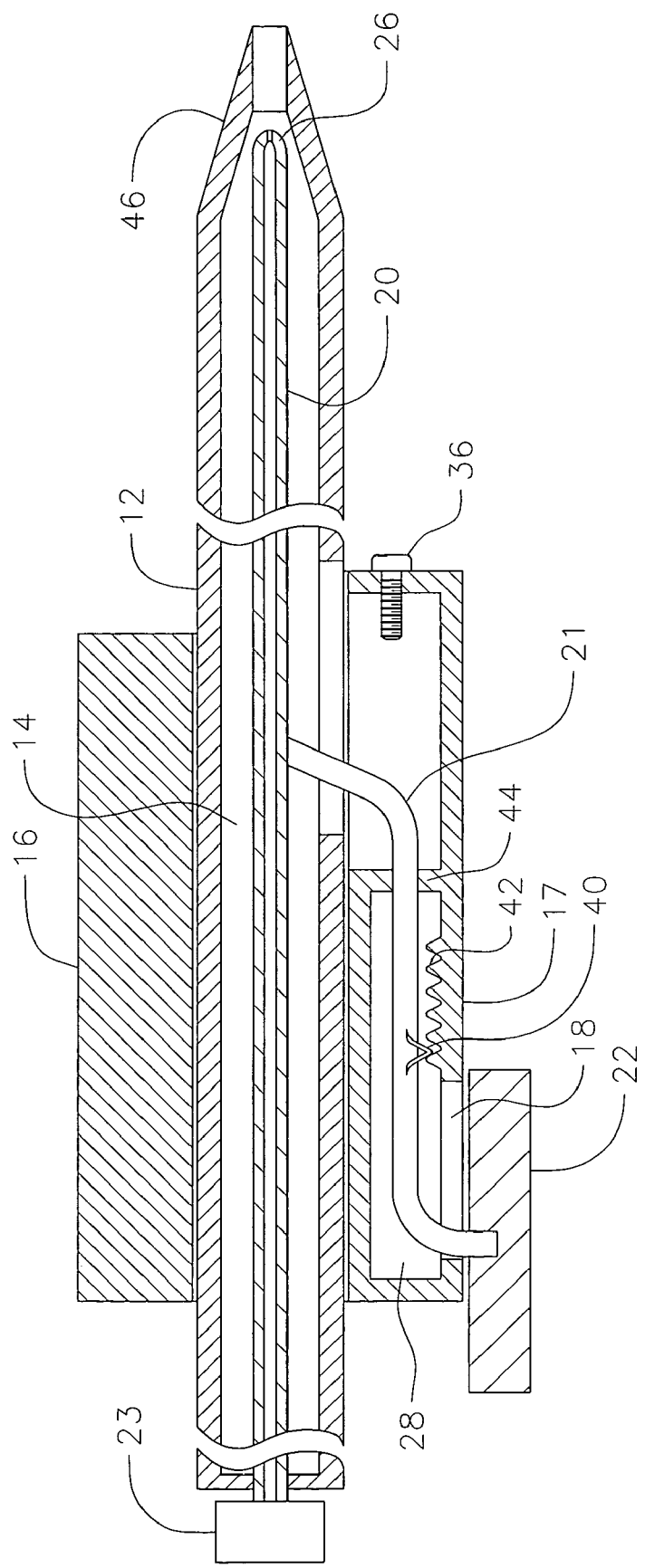
FIG. 3 is a perspective view of an alternative embodiment of a dilator according to the invention.

An alternative embodiment of a dilator according to the current invention is shown in FIG. 3. In this embodiment, a spring 40 extends outwardly from a portion of the arm 21 that is within the channel 28 and mates with any one of a plurality of ridges 42, which are attached to or formed in the channel of the handle 16, such that the arm can be held in position between any two adjacent ridges 42. A shoulder 44 may be positioned adjacent to the plurality of ridges to define a maximum protrusion of the needle tip 26. This embodiment provides the advantage of allowing the operator to move the needle in controlled incremental movements. For example, each ridge 42 may be spaced apart by 1 mm, 5 mm, 1 cm, 5 cm or any other suitable dimension such that with each movement of the thumb control 22, from one ridge to the next, the operator knows the exact length of protrusion of the needle 26 tip from the distal end 46 of the dilator body 12.

An advantage of the dilator of the current invention is that a maximum protrusion length of the needle tip 26 from the distal end 46 of the dilator body 12 may be predetermined. There are a variety of ways in which the maximum protrusion length of the needle tip 26 may be controlled. For example, the proximal end of the handle slot 18 may define the maximum protraction of the needle tip 26 from the distal end 46 of the dilator body 12, while the distal end of the handle slot may define a maximum protrusion of the needle tip from the distal end of the dilator body. Alternatively, the maximum protrusion of the needle tip from the distal end of the dilator body may be defined by a shoulder, such as shoulder 34 or 44, which prevents further distal motion of the arm 21, and therefore the needle 20 as well.

The maximum protrusion of the needle tip 26 may also be variably controlled such that the operator can variably adjust the maximum protrusion of the needle tip. For example, as shown in FIG. 3, a stopper 36 may be attached to the handle 16 to prevent further distal motion of the arm 21. In the depicted embodiment, the stopper 36 is a set screw. In use, the operator may variably control the maximum protrusion of the needle tip 26 by threading the set screw 36 further into the handle 16, thus decreasing the distance between the set screw and the arm 21, which decreases the maximum protrusion of the needle tip, or by threading the set screw away from the handle, thus increasing the distance between the set screw and the arm, which increases the maximum protrusion. Of course, if the set screw is threaded too far away from the handle 16, the set screw will no longer impede the distal motion of the arm 21, and either the distal end of the handle slot 18 or the shoulder, 34 or 44, will define the maximum protrusion of the needle tip 26 from the distal end 46 of the dilator body 12.

When the dilator 10 of the current invention is used to puncture an atrial septum, a procedure commonly referred to as a transseptal left heart catheterization, it is preferred that the procedure is performed under fluoroscopy. For example, biplane fluoroscopy allows for an immediate determination of transseptal equipment location in two dimensions. This arrangement may be obtained by positioning a camera in an anteroposterior fashion and a camera in a lateral fashion. With the cameras so positioned, a guidewire, such as a 0.032 inch diameter guidewire, may be positioned within the right atrium of a patient's heart. A guiding sheath may then be passed over the guidewire. An example of a suitable guiding sheath for use in connection with the present invention is the Preface™ Braided Guiding Sheath, commercially available from Biosense Webster, Inc. (Diamond Bar, Calif.). With the guiding sheath in place, the dilator 10 can be passed through the guiding sheath and into the right atrium. In a preferred embodiment, the distal end or tip 46 of the dilator body 12 comprises tungsten or other radiopaque material, which appears dark under fluoroscopy, allowing the distal tip of the dilator to be easily viewed under fluoroscopy. Once the dilator 10 is in the right atrium, a puncture site may be located. The limbus of the fossa ovalis provides a good reference point for locating an optimal puncture site. Often, the ridge of the limbus of the fossa ovalis can be felt by the operator using the distal tip 46 of the dilator 10. Just below the limbus is the central atrial septum, which tends to be the thinnest area of the septum, and is therefore the preferred area to penetrate. When the central atrial septum is located with the distal tip 46 of the dilator 10, the thumb control 22 of the dilator 10 may be moved in the distal direction such that the needle tip 26 is moved into the protruding position. The distal tip 46 of the dilator 10 may be placed directly adjacent to and abutting the central atrial septum before the thumb control 22 is moved, such that protrusion of the needle tip 26 leads to an immediate puncture of the septum. Alternatively, the distal tip 46 of the dilator 10 may be placed a short distance away from the central atrial septum before the thumb control 22 is moved, such that the operator can move the thumb control in the distal direction until a desired length of protrusion of the needle tip 26 has been obtained, and then advance the entire dilator 10 towards the central atrial septum to puncture the septum. As previously discussed, the proximal end of the needle 20 may be attached to a pressure valve 23 such that the pressure in the needle may be monitored. The pressure in the right atrium is different then the pressure in the left atrium. Therefore, by monitoring the pressure in the needle 20, the operator can determine when the needle has entered the left atrium.

With the distal tip of the needle 20 in the left atrium, the entire dilator 10 is advanced distally to allow the distal end of the dilator to slide through the septum and enter the left atrium. To accomplish this, it is preferred that the distal tip 46 of the dilator 10 is tapered in diameter from the outer diameter of the dilator body 12 to a diameter closer to the outer diameter of the needle 20 as shown in FIGS. 1-3. In addition, when advancing the dilator 10 through the septum, it is helpful to maintain the needle tip 26 in a protruding position to allow the dilator to maintain a smooth transition from the needle diameter to the dilator diameter.

With the distal end of the dilator 10 within the left atrium, the guiding sheath may be advanced over the dilator 10 so that the guiding sheath is in the left atrium. The guiding sheath may then be held in position while the dilator 10 is removed from the patient. The guiding sheath may then be used to guide a therapeutic catheter, such as an ablation catheter, into the left atrium.

The preceding description has been presented with references to presently preferred embodiments of the invention. Persons skilled in the art and technology to which this invention pertains will appreciate that alterations and changes in the described structures can be practiced without meaningfully departing from the principle, spirit and scope of this invention. Accordingly, the foregoing description should not be read as pertaining only to the precise structures described and shown in the accompanying drawings, but rather should be read as consistent with and as support for the following claims, which are to have their fullest and fairest scope.

The invention claimed is:

1. A method for puncturing the atrial septum of a patient comprising:
   inserting into the right atrium of the patient a distal end of a dilator comprising:
      an elongated dilator body having a proximal end, a distal end and at least one lumen extending longitudinally therethrough,
      a handle mounted at the proximal end of the dilator body, the handle comprising a side wall and an opening in the side wall,
      a control button slidably connected to the outside of the handle,
      a needle extending through the lumen of the dilator body, having a distal end comprising a needle tip section and a proximal end, and
      an arm connecting the control button to the needle, the arm being fixedly connected at one end to the control button and fixedly connected at the other end to the needle, the end of the arm connected to the control button extending through an opening in the side wall of the handle, the end of the arm connected to the needle extending through an elongated slot in a longitudinal side of the dilator body and into the lumen in the dilator body, wherein the arm is longitudinally slidable within the elongated slot in the longitudinal side of the dilator body,
      a stopper attached to the handle distal the arm to limit movement of the arm distal the stopper, wherein a position of the stopper relative to the arm is adjustable,
      wherein distal movement of the control button relative to the handle and dilator body causes the needle to move from a retracted position, wherein the needle tip is disposed within the lumen of the dilator body, to a protruding position, wherein the needle tip protrudes beyond the distal end of the dilator body;
   locating, with the distal end of the dilator body, a position on the atrial septum to be punctured;
   advancing the needle tip distally beyond the distal end of the dilator body; and
   puncturing the atrial septum with the needle tip.

2. The method of claim 1, further comprising advancing the distal end of the dilator body into the left atrium after the needle tip has punctured the atrial septum.

3. The method of claim 2, further comprising advancing a distal end of a guiding sheath over the dilator body and into the left atrium after the distal end of the dilator body has been advanced into the left atrium, and removing the dilator body while keeping the sheath in the left atrium after the sheath has entered the left atrium.

4. The method of claim 1, further comprising variably controlling a maximum protrusion length of the needle tip beyond the distal end of the dilator body.

5. The method of claim 1, further comprising incrementally controlling the protrusion length of the needle tip beyond the distal end of the dilator body.

6. The method of claim 1, wherein the needle tip is locked into the retracted position during the inserting of the distal end of the dilator into the right atrium and the locating of the position on the atrial septum to be punctured.

7. The method of claim 1, wherein the needle is hollow and the proximal end of the needle extends beyond the proximal end of the dilator body.

8. A method for puncturing the atrial septum of a patient comprising:
   inserting into the right atrium of the patient a distal end of a dilator comprising:
      an elongated dilator body having a proximal end, a distal end and at least one lumen extending longitudinally therethrough,
      a handle mounted at the proximal end of the dilator body,
      a control button slidably connected to the outside of the handle,
      a needle extending through the lumen of the dilator body, having a distal end comprising a needle tip section and a proximal end, and
      an arm connecting the control button to the needle, the arm being fixedly connected at one end to the control button and fixedly connected at the other end to the needle, the end of the arm connected to the control button extending though an opening in the side wall of the handle, the end of the arm connected to the needle extending through an elongated slot in a longitudinal side of the dilator body and into the lumen in the dilator body, wherein the arm is longitudinally slidable within the elongated slot in the longitudinal side of the dilator body,
      wherein distal movement of the control button relative to the handle and dilator body causes the needle to move from a retracted position, wherein the needle tip is disposed within the lumen of the dilator body, to a protruding position, wherein the needle tip protrudes beyond the distal end of the dilator body;
   locating, with the distal end of the dilator body, a position on the atrial septum to be punctured;
   advancing the needle tip distally beyond the distal end of the dilator body;
   puncturing the atrial septum with the needle tip; and
   variably controlling a maximum protrusion length of the needle tip beyond the distal end of the dilator body by use of a set screw positioned distal the arm, wherein the set screw limits movement of the arm distal the set screw, and a position of the set screw relative to the arm is adjustable.

9. A method for puncturing the atrial septum of a patient comprising:
   inserting into the right atrium of the patient a distal end of a dilator comprising:
      an elongated dilator body having a proximal end, a distal end and at least one lumen extending longitudinally therethrough,
      a handle mounted at the proximal end of the dilator body,
      a control button slidably connected to the outside of the handle,
      a needle extending through the lumen of the dilator body, having a distal end comprising a needle tip section and a proximal end, and
      an arm connecting the control button to the needle, the arm being fixedly connected at one end to the control button and fixedly connected at the other end to the needle, the end of the arm connected to the control button extending through an opening in the side wall of the handle, the end of the arm connected to the needle extending through an elongated slot in a longitudinal side of the dilator body and into the lumen in the dilator body, wherein the arm is longitudinally slidable within the elongated slot in the longitudinal side of the dilator body,
      a stopper attached to the handle distal the arm to limit movement of the arm distal the stopper, wherein a position of the stopper relative to the arm is adjustable;

wherein distal movement of the control button relative to the handle and dilator body causes the needle to move from a retracted position, wherein the needle tip is disposed within the lumen of the dilator body, to a protruding position, wherein the needle tip protrudes beyond the distal end of the dilator body;

locating, with the distal end of the dilator body, a position on the atrial septum to be punctured;

advancing the needle tip distally beyond the distal end of the dilator body;

puncturing the atrial septum with the needle tip; and incrementally controlling the protrusion length of the needle tip beyond the distal end of the dilator body by use of a plurality of ridges attached to the handle that mate with a spring attached to the arm.

10. A method for puncturing the atrial septum of a patient comprising:

inserting into the right atrium of the patient a distal end of a dilator comprising:

an elongated dilator body having a proximal end, a distal end and at least one lumen extending longitudinally therethrough, a handle mounted at the proximal end of the dilator body, a control button slidably connected to the outside of the handle, a needle extending through the lumen of the dilator body, having a distal end comprising a needle tip section and a proximal end, and an arm connecting the control button to the needle, the arm being fixedly connected at one end to the control button and fixedly connected at the other end to the needle, the end of the arm connected to the control button extending through an opening in the side wall of the handle, the end of the arm connected to the needle extending through an elongated slot in a longitudinal side of the dilator body and into the lumen in the dilator body, wherein the arm is longitudinally slidable within the elongated slot in the longitudinal side of the dilator body, a stopper attached to the handle distal the arm to limit movement of the arm distal the stopper, wherein a position of the stopper relative to the arm is adjustable, wherein distal movement of the control button relative to the handle and dilator body causes the needle to move from a retracted position, wherein the needle tip is disposed within the lumen of the dilator body, to a protruding position, wherein the needle tip protrudes beyond the distal end of the dilator body;

locating, with the distal end of the dilator body, a position on the atrial septum to be punctured;

advancing the needle tip distally beyond the distal end of the dilator body; and puncturing the atrial septum with the needle tip, wherein the control button is biased in a proximal direction such that the needle is biased in the retracted position during the inserting of the distal end of the dilator into the right atrium and the locating of the position on the atrial septum to be punctured.

11. The method of claim 10, wherein the proximal end of the arm comprises a shoulder and the handle comprises an internal channel that houses the arm shoulder and a spring, such that the spring applies a force to the arm shoulder to bias the needle in the retracted position.

12. A method for puncturing the atrial septum of a patient comprising:

inserting into the right atrium of the patient a distal end of a dilator comprising:

an elongated dilator body having a proximal end, a distal end and at least one lumen extending longitudinally therethrough, a handle mounted at the proximal end of the dilator body, a control button slidably connected to the outside of the handle, a needle extending through the lumen of the dilator body, having a distal end comprising a needle tip section and a proximal end, the needle being hollow and the proximal end of the needle extending beyond the proximal end of the dilator body, a pressure valve attached to the needle at or near the needle's proximal end, and an arm connecting the control button to the needle, the arm being fixedly connected at one end to the control button and fixedly connected at the other end to the needle, the end of the arm connected to the control button extending through an opening in the side wall of the handle, the end of the arm connected to the needle extending through an elongated slot in a longitudinal side of the dilator body and into the lumen in the dilator body, wherein the arm is longitudinally slidable within the elongated slot in the longitudinal side of the dilator body, a stopper attached to the handle distal the arm to limit movement of the arm distal the stopper, wherein a position of the stopper relative to the arm is adjustable, wherein distal movement of the control button relative to the handle and dilator body causes the needle to move from a retracted position, wherein the needle tip is disposed within the lumen of the dilator body, to a protruding position, wherein the needle tip protrudes beyond the distal end of the dilator body;

locating, with the distal end of the dilator body, a position on the atrial septum to be punctured;

advancing the needle tip distally beyond the distal end of the dilator body; and puncturing the atrial septum with the needle tip.

13. The method of claim 12, further comprising monitoring the pressure in the needle.

* * * * *

UNITED STATES PATENT AND TRADEMARK OFFICE
CERTIFICATE OF CORRECTION

| | |
|---|---|
| PATENT NO. | : 7,618,430 B2 |
| APPLICATION NO. | : 10/118679 |
| DATED | : November 17, 2009 |
| INVENTOR(S) | : Mark S. Scheib et al. |

It is certified that error appears in the above-identified patent and that said Letters Patent is hereby corrected as shown below:

Column 8, Claim 8, line 16        Delete "though"

Insert -- through --

Signed and Sealed this

Third Day of August, 2010

David J. Kappos
*Director of the United States Patent and Trademark Office*